(12) United States Patent
Gagnon

(10) Patent No.: US 8,502,154 B2
(45) Date of Patent: Aug. 6, 2013

(54) METHOD AND SYSTEM FOR ORGAN SPECIFIC PET IMAGING

(75) Inventor: Daniel Gagnon, Twinsburg, OH (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 98 days.

(21) Appl. No.: 13/091,746

(22) Filed: Apr. 21, 2011

(65) Prior Publication Data

US 2012/0271164 A1 Oct. 25, 2012

(51) Int. Cl.
*G01T 1/164* (2006.01)

(52) U.S. Cl.
USPC .................................... 250/363.03

(58) Field of Classification Search
USPC ..... 600/415, 427; 382/132, 289; 250/363.03
See application file for complete search history.

(56) References Cited

U.S. PATENT DOCUMENTS

| | | | |
|---|---|---|---|
| 5,798,527 | A | 8/1998 | Muehllehner et al. |
| 6,455,856 | B1 | 9/2002 | Gagnon |
| 6,946,658 | B2 | 9/2005 | Tai |
| 7,103,233 | B2 * | 9/2006 | Stearns .......................... 382/289 |
| 2004/0004188 | A1 | 1/2004 | Tai |
| 2006/0106306 | A1 | 5/2006 | Essner et al. |
| 2008/0029704 | A1 | 2/2008 | Hefetz et al. |
| 2008/0185527 | A1 | 8/2008 | Van Dulmen et al. |
| 2008/0230704 | A1 | 9/2008 | Daghighian |
| 2008/0296505 | A1 | 12/2008 | Cooke et al. |
| 2010/0010343 | A1 | 1/2010 | Daghighian et al. |
| 2010/0219346 | A1 | 9/2010 | Daghighian |
| 2011/0062340 | A1 | 3/2011 | Gagnon |

FOREIGN PATENT DOCUMENTS

| | | |
|---|---|---|
| JP | 2000-221272 | 8/2000 |
| JP | 2005-532571 | 10/2005 |
| JP | 2007-163373 | 6/2007 |
| JP | 2007-202976 | 8/2007 |
| JP | 2007-212295 | 8/2007 |
| JP | 2008-39776 | 2/2008 |
| JP | 2008-533455 | 8/2008 |
| JP | 2009-31306 | 2/2009 |
| JP | 2011-59099 | 3/2011 |

OTHER PUBLICATIONS

Thomas Beyer, A Combined PET/CT Scanner for Clinical Oncology, 2000, J Nucl Med, 41:1369-1379.*

(Continued)

*Primary Examiner* — Tse Chen
*Assistant Examiner* — Rochelle Reardon
(74) *Attorney, Agent, or Firm* — Oblon, Spivak, McClelland, Maier & Neustadt, L.L.P.

(57) ABSTRACT

An imaging system, including (1) a CT scanner configured to scan an object arranged on a patient pallet; (2) a PET scanner, including a first detector portion, including first detector elements, arranged circumferentially around the patient pallet, the first detector portion having a predetermined axial extent and transaxially subtending less than 360 degrees with respect to a central axis of the scanner; and a second detector portion, including second detector elements, arranged separately from and opposing the first detector portion, wherein the second detector elements are of a different type than the first detector elements, and the second detector portion is configured to be movable radially and circumferentially around the object; and (3) an acquisition subsystem configured to acquire first event data from the first detector portion and to acquire second event data from the second detector portion.

10 Claims, 14 Drawing Sheets

(56) References Cited

OTHER PUBLICATIONS

Yuan-Chuan Tai et al., "Initial Study of an Asymmetric PET System Dedicated to Breast Cancer Imaging", IEEE Transactions on Nuclear Science, vol. 53, No. 1, Feb. 2006, pp. 121-126.
U.S. Appl. No. 13/091,761, filed Apr. 21, 2011, Gagnon.
U.S. Appl. No. 13/091,722, filed Apr. 21, 2011, Gagnon.
Office Action mailed Jun. 13, 2012, in co-pending U.S. Appl. No. 13/091,761.
International Search Report issued May 22, 2012, in PCT/JP2012/060791 (with English-language translation).
International Search Report issued Jul. 31, 2012, in PCT/JP2012/060788.
International Search Report issued May 22, 2012, in PCT/JP2012/060787 (with English-language translation).
Office Action mailed Mar. 15, 2013 in co-pending U.S. Appl. No. 13/091,722.

* cited by examiner

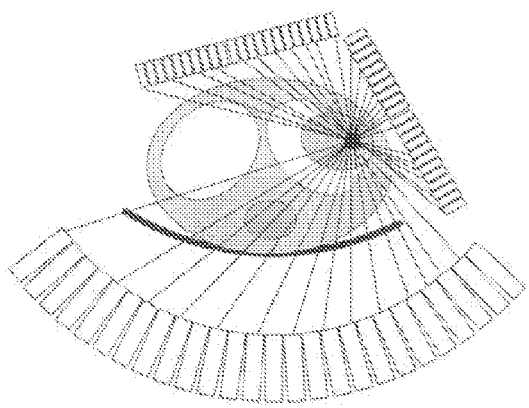 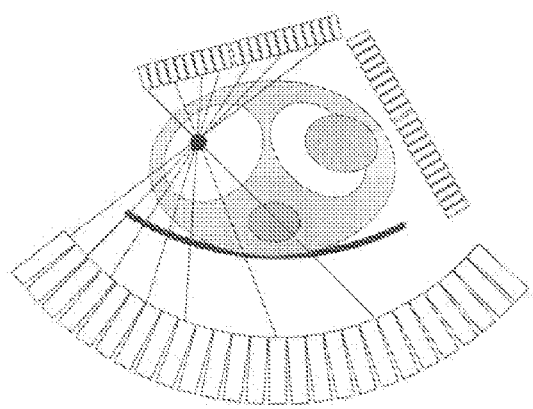
FIG. 10A                    FIG. 10B

METHOD AND SYSTEM FOR ORGAN SPECIFIC PET IMAGING

CROSS-REFERENCE TO RELATED APPLICATIONS

This application is related to the applications entitled "New Geometry for PET Imaging" Ser. No. 13/091,761 and "PET Imaging System Including Detector Elements of Different Design and Performance" 13/091,722, both of which were filed on the same date as the present application. The contents of the above-identified applications are incorporated herein by reference.

FIELD

Embodiments disclosed herein generally relate to a positron emission tomography/computed tomography (PET/CT) scanner, and in particular, to new scanner geometries for organ-specific PET/CT imaging.

BACKGROUND

The use of positron emission tomography is growing in the field of medical imaging. In PET imaging, a radiopharmaceutical agent is introduced into the object to be imaged via injection, inhalation, or ingestion. After administration of the radiopharmaceutical, the physical and bio-molecular properties of the agent will concentrate at specific locations in the human body. The actual spatial distribution of the agent, the intensity of the region of accumulation of the agent, and the kinetics of the process from administration to eventually elimination are all factors that may have clinical significance. During this process, a positron emitter attached to the radiopharmaceutical agent will emit positrons according to the physical properties of the isotope, such as half-life, branching ratio, etc.

The radionuclide emits positrons, and when an emitted positron collides with an electron, an annihilation event occurs, wherein the positron and electron are destroyed. Most of the time, an annihilation event produces two gamma rays at 511 keV traveling at substantially 180 degrees apart.

By detecting the two gamma rays, and drawing a line between their locations, i.e., the line-of-response (LOR), one can retrieve the likely location of the original disintegration. While this process will only identify a line of possible interaction, by accumulating a large number of those lines, and through a tomographic reconstruction process, the original distribution can be estimated. In addition to the location of the two scintillation events, if accurate timing (within few hundred picoseconds) is available, a time-of-flight (TOF) calculation can add more information regarding the likely position of the event along the line. Limitations in the timing resolution of the scanner will determine the accuracy of the positioning along this line. Limitations in the determination of the location of the original scintillation events will determine the ultimate spatial resolution of the scanner, while the specific characteristics of the isotope (e.g., energy of the positron) will also contribute (via positron range and co-linearity of the two gamma rays) to the determination of the spatial resolution the specific agent.

The collection of a large number of events creates the necessary information for an image of an object to be estimated through tomographic reconstruction. Two detected events occurring at substantially the same time at corresponding detector elements form a line-of-response that can be histogrammed according to their geometric attributes to define projections, or sinograms to be reconstructed. Events can also be added to the image individually.

The fundamental element of the data collection and image reconstruction is therefore the LOR, which is the line traversing the system-patient aperture. Additional information can be obtained regarding the location of the event. First, it is known that, through sampling and reconstruction, the ability of the system to reconstruct or position a point is not space-invariant across the field of view, but is better in the center, slowly degrading toward the periphery. A point-spread-function (PSF) is typically used to characterize this behavior. Tools have been developed to incorporate the PSF into the reconstruction process. Second, the time-of-flight, or time differential between the arrival of the gamma ray on each detector involved in the detection of the pair, can be used to determine where along the LOR the event is more likely to have occurred.

The above described detection process must be repeated for a large number of annihilation events. While each imaging case must be analyzed to determine how many counts (i.e., paired events) are required to support the imaging task, current practice dictates that a typical 100-cm long, FDG (fluoro-deoxyglucose) study will accumulate several hundred million counts. The time required to accumulate this number of counts is determined by the injected dose of the agent and the sensitivity and counting capacity of the scanner.

PET imaging systems use detectors positioned across from one another to detect the gamma rays emitting from the object. Typically a ring of detectors is used in order to detect gamma rays coming from each angle. Thus, a PET scanner is typically substantially cylindrical to be able to capture as much radiation as possible, which should be, by definition, isotropic. The use of partial rings and rotation of the detector to capture missing angles is also possible, but these approaches have severe consequences for the overall sensitivity of the scanner. In a cylindrical geometry, in which all gamma rays included in a plane have a chance to interact with the detector, an increase in the axial dimension has a very beneficial effect on the sensitivity or ability to capture the radiation. Thus, the best design is that of a sphere, in which all gamma rays have the opportunity to be detected. Of course, for application to humans, the spherical design would have to be very large and thus very expensive. Accordingly, a cylindrical geometry, with the axial extent of the detector being a variable, is realistically the starting point of the design of a modern PET scanner.

Once the overall geometry of the PET scanner is known, another challenge is to arrange as much scintillating material as possible in the gamma ray paths to stop and convert as many gamma rays as possible into light. It is necessary to consider two dimensions of optimization in this process. On one hand, the "in-plane" sensitivity forces as much crystal as possible (crystal thickness) around the circumference of the detector. On the other hand, for a given crystal thickness, the axial length of the detector-cylinder will define the overall system sensitivity, which is roughly proportional to the square of the axial length (the solid angle subtended by a point in the middle of a cylinder). Practical cost considerations will unavoidably be part of the optimization process. Optimal distribution of the crystal and associated sensors is central to the overall system cost, as it typically represents up to two-thirds of the entire cost of the PET imaging system.

Conventionally, a cylindrical geometry is the design of choice for a PET scanner. As shown in FIG. 1, the cylindrical geometry can capture all events in the transaxial plane. The axial extent of the detector will determine how many such planes can be defined, as well as how many oblique planes can be utilized.

As shown in FIG. 1, the scanner is formed by a series of small blocks representing the detector elements. Only a few dozen detector elements are shown for simplicity. In reality, several hundred pixels are necessary to adequately sample the geometry. The same is true for the axial direction. Detector elements are typically the same size in both directions, but can also be of different sizes in the two dimensions. The cross-section of the patient shows a thorax, lungs, heart, and spine, wherein the patient is resting on the scanner patient pallet. The drawings further illustrates a few possible lines of response, representing positron annihilation events originating from the "heart" and being collected at various points on the scanner, both on the circumference and axially.

The overall dimension of the scanner typically varies from 70 to 90 cm in diameter so as to cover the whole human body. The axial dimension can vary more. Conventional scanners have at least 15 cm of axial coverage (to at least cover the heart), while larger dimensions are possible and desirable.

Further, current clinical practice places the patient more or less in the center of the scanner. Given that the patient typically comprises 50% or less of the scanner diameter, placing the patient slightly lower than the center is also desirable, providing more "breathing" space for the patient inside the scanner aperture.

Nevertheless, the goal of the PET scanner is to collect as many lines as possible from the patient in both the axial and transaxial planes.

While the conventional design provides an efficient geometry to collect positron annihilation events, it also defines a rigid set of rules for building the scanner, and consequently, offers few options for controlling its cost.

Attempts to increase the axial extent of the scanner have been proposed, but the rules for complete sampling in the transaxial plane have not changed.

Given the very high relative cost of the detector elements, any attempts to increase the scanner aperture (i.e., a larger diameter) or its axial extent require a significant cost increase. An increase in the diameter of the scanner is desirable to accommodate positioning (immobilization) tools for therapy (matching the radiation therapy unit), which require 85 cm or more, and also to provide better patient comfort by diminishing the claustrophobic stress still experienced by many patients. An increase in the axial extent of the scanner is desirable to increase the sensitivity (number of events being collected) and to cover larger organ or body sections. For example, the entire lung typically spans up to 25-30 cm and the head and neck requires at least 30 cm.

Thus, a real question facing scanner designers is, given a certain amount of detector material, which represents the predominant cost of the scanner, what geometry optimizes the number of event counts while providing adequate sampling for reconstruction.

Additionally, conventional designs do not provide a way to change or otherwise optimize the scanner for scanning a specific organ or region of interest in the patient. Rather, all images are acquired in the same way, regardless of the object or region of the object to be optimized.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 10A and 10B illustrate an embodiment in which flat top scanners are positioned based upon a region of interest to be scanned;

DETAILED DESCRIPTION

Figure 1:
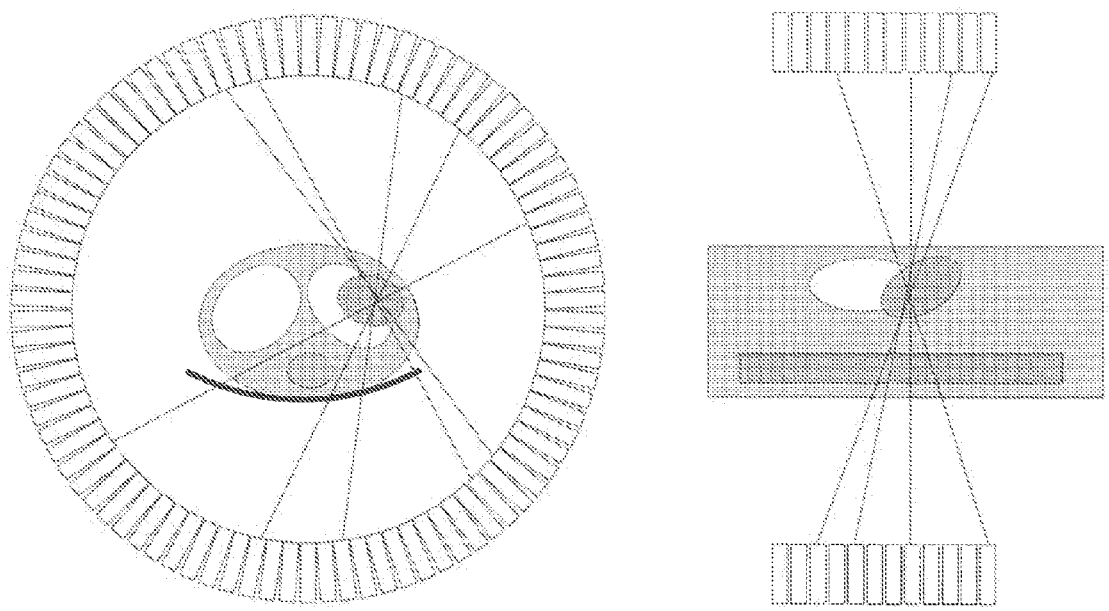
FIG. 1 illustrates conventional full-ring PET scanner.

Embodiments described herein are directed to new scanner geometries to optimize positron annihilation event collection.

According to one embodiment, a positron emission tomography (PET) scanner includes (1) a first detector portion arranged circumferentially around a patient pallet, the first detector portion having a predetermined axial extent and transaxially subtending more than 180 degrees, but less than 360 degrees with respect to a central axis of the scanner defined by the first detector portion; and (2) a second detector portion arranged separately from and opposing the first detector section, the second detector portion having a radius of curvature smaller than a radius of curvature of the first detector portion, wherein the second detector portion transaxially subtends less than 180 degrees with respect to the central axis of the scanner.

In another embodiment, the second detector portion transaxially subtends at least 30 degrees with respect to the central axis of the scanner.

In another embodiment, the sum of angles transaxially subtended by the first and second detector portions with respect to the central axis of the scanner is substantially less than 360 degrees.

In another embodiment, the sum of angles transaxially subtended by the first and second detector portions with respect to the central axis of the scanner is more than 360 degrees.

In another embodiment, the second detector portion is arranged closer to the central axis than the first detector portion. For example, the second detector portion is arranged closer to the central axis than the first detector portion by at least 10% of a radius of the first detector portion.

In another embodiment, the first detector includes a plurality of first detector elements, the second detector includes a plurality of second detector elements, and each of the second detector elements has a smaller detection surface than the first detector elements.

In another embodiment, the second detector portion is flat.

In another embodiment, a third detector portion is arranged to oppose the first detector portion.

In another embodiment, the second and third detector portions are flat and have detector elements that each have a smaller detection surface than detection surfaces of detector elements of the first detector portion.

In another embodiment, the second detector portion is arranged directly below and touching the patient pallet.

In another embodiment, the second detector portion is arranged above the patient pallet.

In another embodiment, the second detector portion is configured to be movable tangentially and radially.

In another embodiment, the first and second detector portions are configured to be rotated around the patient pallet to any axial angle.

In an alternative embodiment, a positron emission tomography scanner includes (1) a first detector portion arranged circumferentially around a patient pallet, the first detector portion having a predetermined axial extent and transaxially subtending less than 360 degrees with respect to a central axis of the scanner defined by the first detector portion, wherein the first detector portion includes a plurality of first detector elements; and (2) a second detector portion arranged separately from and opposing the first detector section, the second detector portion including a plurality of second detector elements, the second detector elements being of a different type than the first detector elements, wherein each of the first detector elements includes photomultiplier tubes (PMTs); and each of the second detector elements includes photosensors of a different type from the PMTs of the first detector elements. For example, each of the second detector elements includes a solid state photosensor such as a silicon photomultiplier (SiPM). Alternatively, each of the second detector elements includes an avalanche photodiode (APD).

In another embodiment, each of the first detector elements includes a scintillation crystal having a first thickness and a first pixel surface area and each of the second detector elements includes a scintillation crystal having a second thickness different from the first thickness.

In another embodiment, each of the second detector elements includes a scintillation crystal having a second pixel surface area different from the first pixel surface area.

In another embodiment, a positron emission tomography (PET) scanner includes: (1) a first detector portion arranged circumferentially around a patient pallet, the first detector portion having a predetermined axial extent and transaxially subtending less than 360 degrees with respect to a central axis of the scanner defined by the first detector portion, wherein the first detector portion includes a plurality of first detector elements; and (2) a second detector portion arranged separately from and opposing the first detector section, the second detector portion including a plurality of second detector elements, wherein the second detector portion is configured to having different imaging properties than the first detector portion. For example, in one embodiment, the second detector portion is configured to have at least one of a timing resolution, an energy resolution, and sensitivity different from that of the first detector portion.

In another embodiment, a positron emission tomography (PET) scanner includes (1) a first detector portion arranged circumferentially around a patient pallet, the first detector portion having a predetermined axial extent and transaxially subtending less than 360 degrees with respect to a central axis of the scanner defined by the first detector portion, wherein the first detector portion includes a plurality of first detector elements; and (2) a second detector portion arranged separately from and opposing the first detector section, the second detector portion including a plurality of second detector elements, the second detector elements being of a different type than the first detector elements, wherein an event acceptance window for the first detector portion is different than an event acceptance window for the second detector portion.

In an alternative embodiment, an imaging system includes (1) a computed tomography (CT) scanner configured to scan an object arranged on a patient pallet; (2) a positron emission tomography (PET) scanner, including (a) a first detector portion, including first detector elements, arranged circumferentially around the patient pallet, the first detector portion having a predetermined axial extent and transaxially subtending less than 360 degrees with respect to a central axis of the scanner; and (b) a second detector portion, including second detector elements, arranged separately from and opposing the first detector portion, wherein the second detector elements are of a different type than the first detector elements, and the second detector portion is configured to be movable radially and circumferentially around the object; and (3) an acquisition subsystem configured to acquire first event data from the first detector portion, to acquire second event data from the second detector portion, and to transmit the acquired first and second event data to a data processing system for analysis and reconstruction.

In another embodiment, the imaging system further includes a controller configured to (1) cause the CT scanner to scan the object to obtain CT image data of the object, (2) obtain an axial extent of a region of interest within the object using a projection image obtained from the CT image data; (3) obtain a location of the region of interest obtained using a transaxial image obtained from the CT image data; (4) cause the patient pallet to be positioned longitudinally based on the obtained axial extent of the region of interest; and (5) cause the second detector portion to be moved at least one of radially and circumferentially based on the identified location of the region of interest. Further, in one embodiment, the controller is further configured to cause a PET scan of the object to be performed after the patient pallet has been positioned longitudinally and the second detector portion has been moved at least one of radially and circumferentially.

In another embodiment, the imaging system further includes a mechanical subsystem configured to move the patient pallet longitudinally in response to a command received from the controller, and a detector positioning unit configured to move the second detector portion at least one of radially and circumferentially in response to at least one command received from the controller.

In another embodiment, the imaging system further includes a data processing system configured to reconstruct an image of the region of interest of the object based on the acquired first and second event data.

In another embodiment, the PET scanner further includes a third detector portion, including third detector elements, arranged separately from and opposing the first detector section, wherein the third detector elements are of a different type than the first detector elements, and the third detector portion is configured to be movable radially and circumferentially around the object, wherein the acquisition subsystem is configured to acquire third event data from the third detector portion, and to transmit the acquired first, second, and third event data to the data processing system for analysis and reconstruction In another embodiment, there is provided a method of acquiring imaging data of an object arranged on a patient pallet using a computed tomography (CT) scanner configured to scan the object, and a positron emission tomography (PET) scanner that includes a first detector portion arranged circumferentially around the patient pallet, the first detector portion having a predetermined axial extent and transaxially subtending less than 360 degrees with respect to a central axis of the scanner, and a second detector portion arranged separately from and opposing the first detector section, wherein the second detector portion is configured to be movable radially and circumferentially around the object, the method comprising: (1) acquiring CT image data of the object; (2) obtaining, using an image obtained from the acquired CT image data, an axial extent of a region of interest; (3) obtaining, using a transaxial image obtained from the acquired CT image data, a location of the region of interest; (4) automatically positioning the patient pallet longitudinally, based on the obtained axial extent of the region of interest; and (5) automatically moving the second detector portion at least one of radially and circumferentially based on the obtained location of the region of interest.

In another embodiment, the method further includes performing a PET scan of the object to acquire first event data from the first detector portion and second event data from the second detector portion, after the patient pallet has been positioned longitudinally and the second detector has been moved at least one of radially and circumferentially, and reconstructing an image of the region of interest of the object based on the acquired first and second event data.

Figure 2:
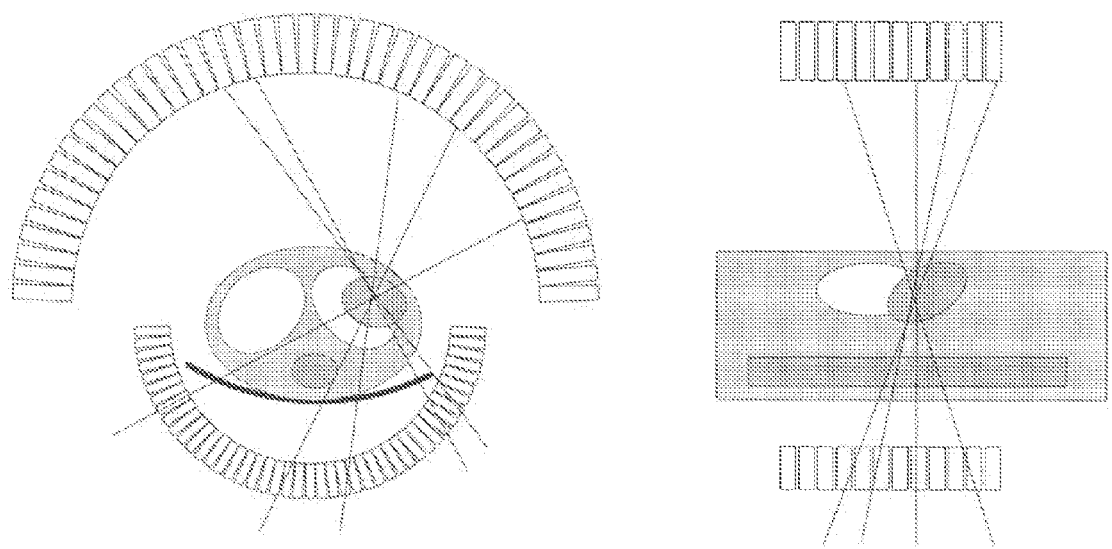
FIG. 2 illustrates a two-half scanner according to one embodiment.

Referring now to the drawings, wherein like reference numerals designate identical or corresponding parts throughout the several views, FIG. 2 illustrates a PET scanner design according to one embodiment. As shown in FIG. 2, the bottom half of the scanner is shrunk to fit the dimension of the patient, which is typically half the diameter of a scanner. By comparison, in the conventional design shown in FIG. 1, the space under the patient pallet is of no utility, not even for patient comfort.

Note that, as shown in FIG. 2, all of the lines of response that would have been collected in the conventional design of FIG. 1 are still collected by the smaller bottom half of the scanner. Further, lines of response that connect a detector element from the top half and the gap in the detector ring, do not cross the patient and are therefore not required to be collected in a scan of the patient. Second, by defining smaller detector elements, which are smaller in proportion to the decrease in the diameter, the same number of possible lines of response exist between the two halves of the detector. Note that the new "two-half" scanner has the same transaxial sensitivity and the same sampling ability as the conventional, full-ring scanner, while providing up to 20-25% savings in detector cost. In addition, the bottom part of the two-half scanner is closer to the object, thus providing an increased axial solid angle (in 3D), and thus an increased sensitivity that can either be used to improve performance or to reduce the amount of crystal thickness, thus providing a further cost savings.

Figure 3A:
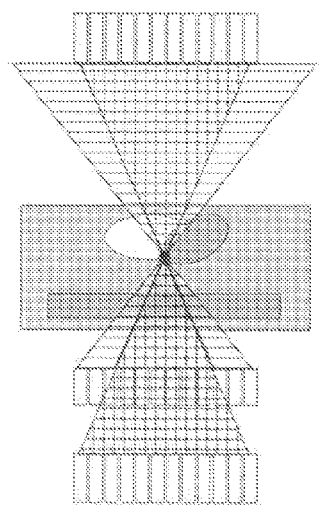
FIGS. 3A-3C illustrate the increase in sensitivity of the embodiment shown in FIG. 2.
Figure 3B:
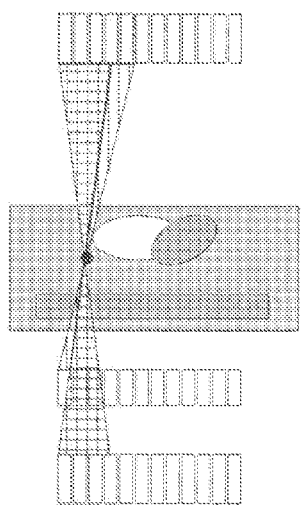
Figure 3C:
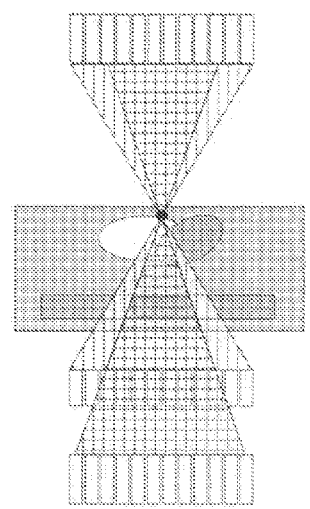

The increase in sensitivity of this embodiment is evident by examining the axial plane with respect to FIGS. 3A-3C. A point source in the middle of the scanner does not produce more coincidence events compared to the conventional ring (shown as the square-patterned section in FIG. 3A) since the additional solid angle from the closer detector (see horizontal line pattern in FIG. 3A) cannot be used to draw additional lines of response from that point, as such lines fall outside the range of the upper detector. However, for other emission points, the gain in sensitivity can be substantial, as illustrated by the vertical line sections of FIGS. 3B and 3C. However, an exact calculation of the "volume sensitivity" would require more complex modeling tools.

The distribution of the acquired counts is also positively affected with the two-half scanner shown in FIG. 2. In the conventional center-ring geometry, the axial sensitivity profile of a line source is a triangle, representing the fact that as you go from the axial center of the scanner toward the edge of the field of view (FOV), there is less and less opportunity to create a coincidence event, as illustrated in the left-hand side of FIG. 4. The fact that the overall system sensitivity goes to zero at the edge of the FOV causes problems for reconstruction, in particular, preventing a constant statistical texture.

Figure 4:
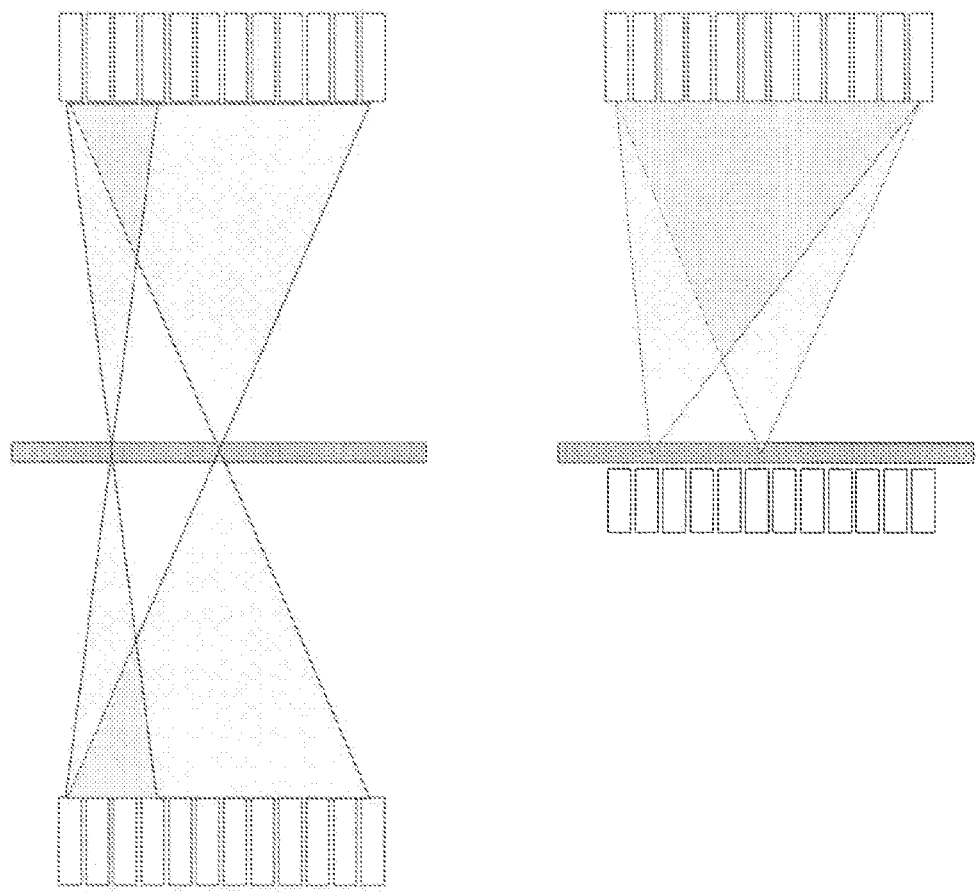
FIG. 4 illustrates the axial sensitivity of the two-half scanner.

In the extreme case shown on the right-hand side of FIG. 4, for a line and zero distance between the source and the bottom detector, all gamma rays going down would be detected and therefore the overall system sensitivity would be simply the solid-angle of the top detector, which exhibits only a slight bulging in the middle of the axial FOV. It is to be assumed that cases in between would progressively depart from the triangular shape towards an almost flat distribution.

Further, while the constant number of possible lines of response guarantees an adequate tomographic reconstruction, the smaller detector elements support a smaller (i.e., better) ultimate spatial resolution. Spatial resolution is model-based, with iterative reconstruction being more or less proportional to the "tube of response," i.e., the volume joining the surface of two detector elements (as opposed to a dimensionless line joining the center of the two detector elements). Moreover, the better spatial resolution can be used to improve imaging performance, or to allow slightly larger detector elements for both the top and bottom parts of the scanner, with fewer, larger crystal elements.

Figure 5:
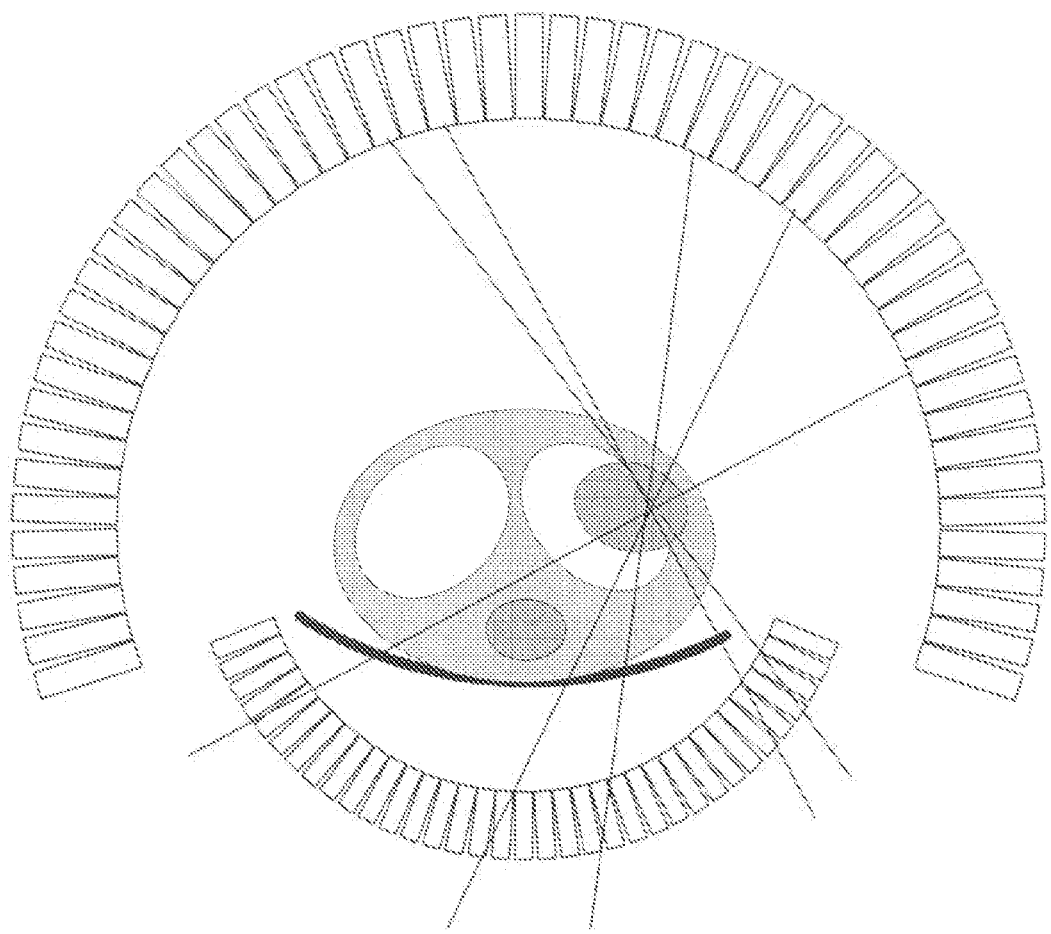
FIG. 5 illustrates a second embodiment of the two-half scanner.
Figure 6:
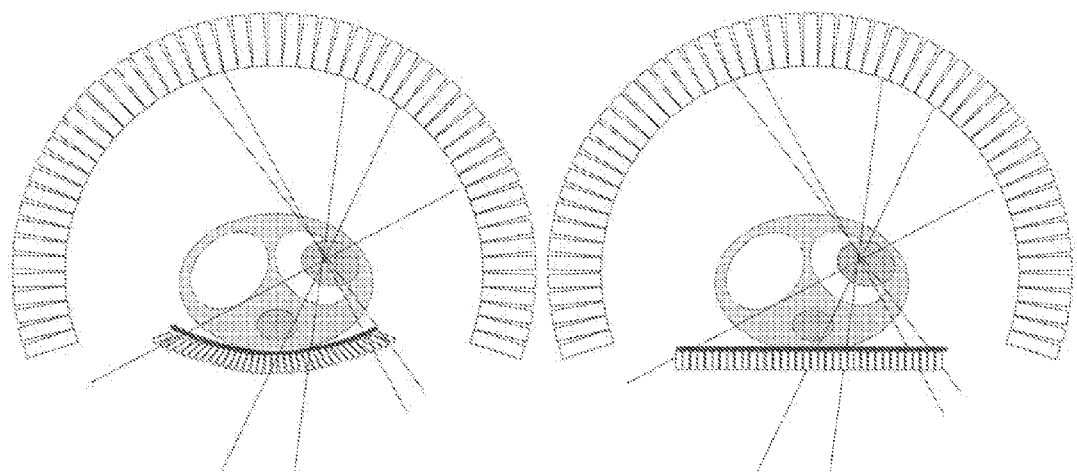
FIGS. 6-9 illustrates additional embodiments of the two-half scanner.

In an alternative embodiment, as shown in FIG. 5, the split between the two halves of the scanner is not exactly equal. To accommodate a larger opening around the patient pallet, different ratios can be implemented. As shown in FIG. 6, all lines are still captured by the new geometry. The impact on the amount of "savings" for a given two-half design can be estimated in the manner described above.

In another embodiment, the smaller ring section can touch the patient pallet and offer even more sensitivity/geometric gain, as shown in FIG. 6 for a curved pallet (on the left) or for a flat pallet (on the right), both of which are of typical use in PET imaging, especially for radiation therapy.

In the above embodiments, segmentation of the ring into two sections is top-down symmetrical. However, in the above embodiment, the smaller bottom half section is placed close to the patient pallet. As shown in the left-hand side of FIG. 7, when a smaller top half section is used, some lines of response are not captured by the geometry. Accordingly, there is a constraint on the vertical position of the two halves when the smaller half section is placed on top, as shown on the right-hand side of FIG. 7.

Figure 7:
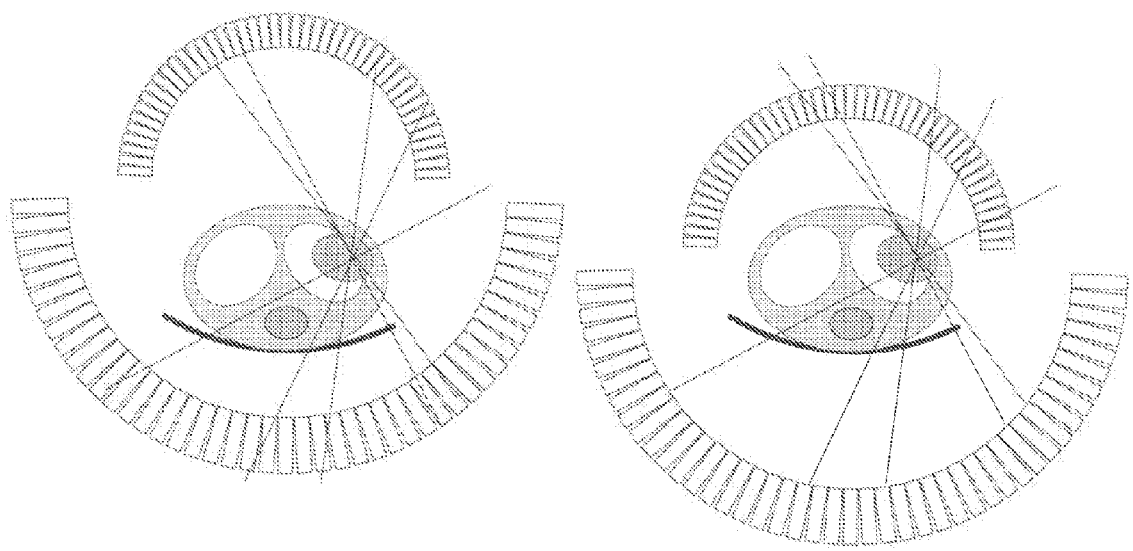

While the right-hand-side of FIG. 7 shows a technically acceptable geometry, in practice, bringing the smaller top portion down that close to the patient (or equivalently bringing the patient pallet up) might create an uncomfortable situation for the patient, particularly when one realizes that FIG. 7 only shows the detector elements without the rest of the detector system (photomultiplier tubes, electronics, supports, cables, etc).

Figure 8:
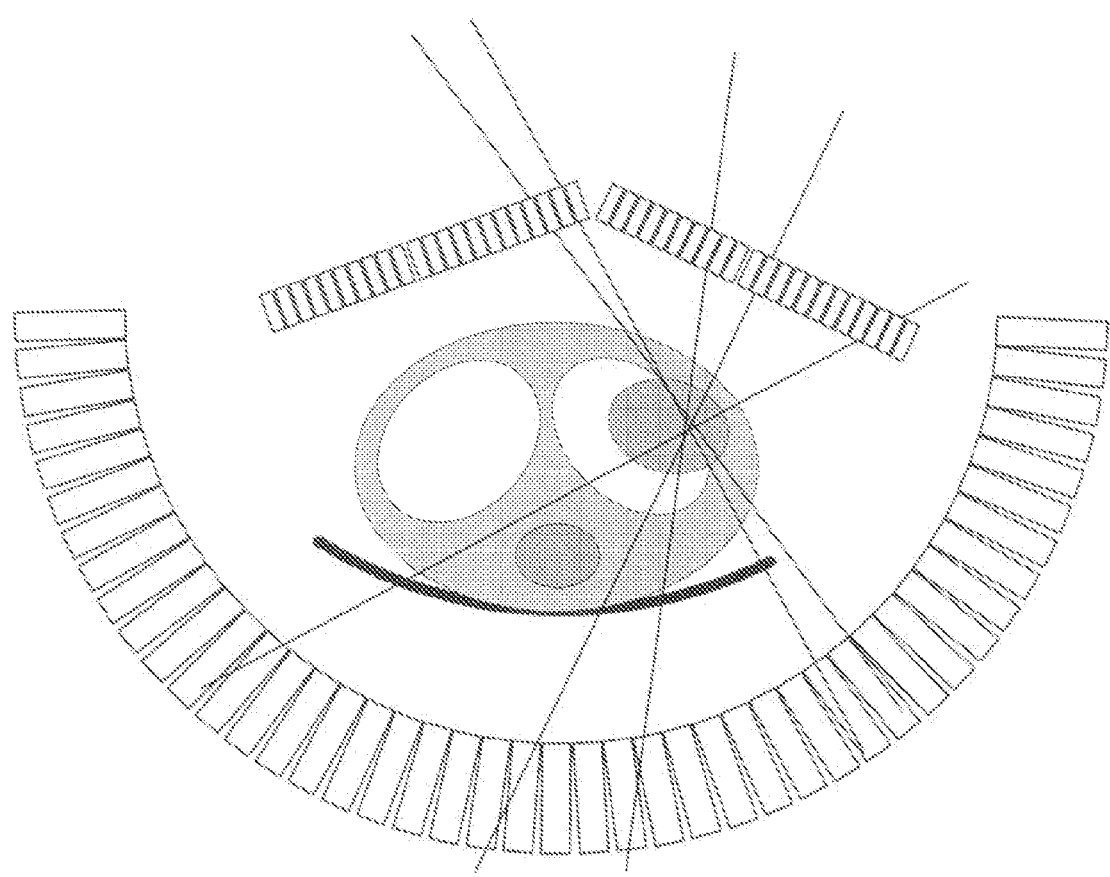

However, in an alternative embodiment, having the smaller section on top is feasible. First, the detector can be composed of a solid-state sensor, such as SiPM (silicon photomultiplier) or APD (avalanche photodiode). With such sensors, the compact nature of the detector would allow for a less impressive detector mass to be used. Second, solid-state-based detectors are movable (unlike the rest of the ring) allowing for the patient to be positioned first, and then bringing the top detector into an imaging position. Third, the top section of the ring can in fact be further segmented into two or more parts to facilitate positioning, and storage when not imaging. Finally, as shown in FIG. 8, similar to the embodiment shown in FIG. 7, some of the detector elements can be arranged in one or more flat, linear sections.

Note also that the various embodiments of the two-part scanner described above, including the top/bottom inversion symmetry, are invariant with respect to rotation. In practice, there would typically be no reason to select anything other than symmetry about the horizontal axis (top/bottom split and inversion), except for regional imaging, such as the heart, or right (or left) breast. In those cases, the availability of a better spatial resolution detector at the proximity of the region of interest or organ can be exploited.

Each of the scanner embodiments described above produce substantially (if not exactly) the same image in the same amount of time as the full-ring geometry, but with a reduction of 20% to 50% of the detection material. Such a reduction can be significant to either improve system performance at the same cost, or to reduce the cost for the same imaging performance.

Note that in each of the two-part geometries described above, lines of response enter the detector element in the smaller section at a greater incidence angle (less perpendicular to the entrance plane) and thus create higher spatial blurring by added parallax error. However, the higher parallax error could at least partially be compensated for by the reduction in crystal thickness due to the much higher solid angle formed by the smaller ring section with respect to the patient.

The same principles can be used to optimize PET imaging, while allowing for some departure from the complete sampling. Time-of-flight (ToF) information can provide enough "local" properties to support quasi-complete imaging conditions and reconstruction in some region of the object, while the imaging would deteriorate progressively away from the region. For example, several important imaging tasks, e.g., cardiac or breast imaging, are clearly focused on gathering information from a relatively small area of the body, as shown in FIGS. 10A and 10B.

FIG. 10A shows that, with two flat-top detectors positioned as shown, the heart receives an almost complete angular sampling providing enough information for an optimal or quasi-optimal reconstruction. As shown in FIG. 10B, a point symmetrically positioned on the other side of the body receives significantly fewer lines of response, showing that, in this geometry for this point, the right detector is completely useless and only a small portion of the bottom detector can be used. However, ToF imaging inherently allows for a better isolation of the two regions. Moreover, when such a PET scanner is part of a hybrid PET/CT or PET/MR scanner, the CT or MR image can be used to identify the region or organ of interest and to optimize the PET detector positioning.

In another embodiment, only one type of detector is ToF capable. First, note that for incomplete sampling, both detectors are clearly required to provide enough timing information for the reconstruction to benefit from the additional information. However, in complete sampling cases, one can see that most of the events come from mixed detectors.

For example, assume that the minimum overall timing resolution to obtain valuable ToF information is 1 ns. (Commercial systems are currently achieving between 500 and 600 ps). When the system is composed of two types of detector designs: (1) a Type A detector capable of 300 ps timing resolution (measured by putting detector A with a perfect, or at least, significantly faster, detector), and (2) a Type B detector only capable of 2 ns (2000 ps). A system built with only a Type A detector would have an overall system timing resolution (using the classical quadratic composition) of SQRT $(300^2+300^2)$, or around 425 ps. A system built only with a Type B detector would be SQRT $(2000^2+2000^2)$ or 2.8 ns or 2,800 ps. However, a system in which most of the events are hybrid Type A and Type B would essentially be controlled by the Type B detector at 2 ns, offering a usable advantage on the front-end detector electronics and image quality.

The performance for most of the attributes when different types of detectors are used would follow the same quadratic composition. However, in the case of energy resolution, different treatments (e.g., acceptance windows) would have to be applied to the different acquisition chain if the difference between the two types is large enough. An energy windowing adjustment will be an important factor in adjusting the sensitivity of the two types of detectors. An energy window matching the intrinsic behavior of each detector is also necessary to make sure the scatter acceptance from both detectors is balanced.

Finally, one skilled in the art would recognize that important modifications would be needed to perform typical calibration tasks on the system. Timing and energy resolution, as well as system normalization, would be more complex.

According to the embodiments described above, a PET scanner includes a first detector portion arranged circumferentially around a patient pallet and a second detector portion arranged separately from and opposing the first detector section. The first detector portion includes a plurality of first detector elements, while the second detector portion including a plurality of second detector elements. As discussed above, the second detector elements can be of a different type than the first detector elements.

For example, in one embodiment, each of the first detector elements includes photomultiplier tubes (PMTs) and a scintillation crystal having a first thickness and a first pixel surface area, while each of the second detector elements has a scintillation crystal having a second thickness different from the first thickness and a second pixel surface area different from the first pixel surface area.

Moreover, in one embodiment, each of the second detector elements includes photosensors different from the PMTs of the first detector elements. For example, in one embodiment, each of the second detector elements includes a solid state photosensor such as a silicon photomultiplier (SiPM).

Moreover, the second detector portion can be configured to have different imaging properties than the first detector portion. For example, in one embodiment, the first and second detector portions have different energy and timing resolution. Further, in another embodiment, an event acceptance window for the first detector portion is different than an event acceptance window for the second detector portion.

PET/CT System

Figure 11:
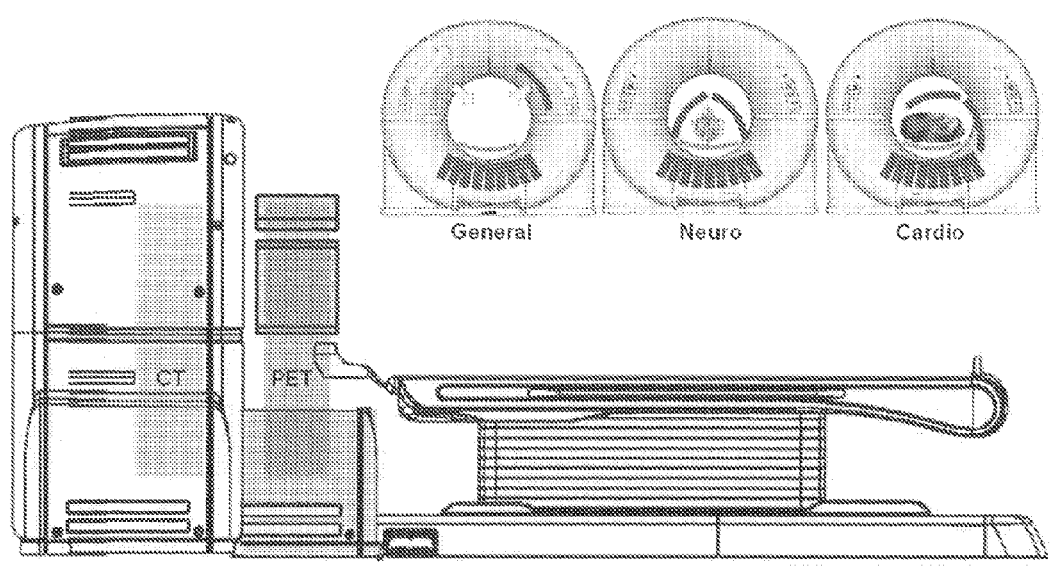
FIGS. 11 and 12A-12C illustrate PET/CT embodiments of the two-half scanner.

The two-half geometries described above can be implemented with existing CT systems in several ways. In a first embodiment, as shown in FIG. 11, the smaller, movable, solid-state detectors are arranged on top of the patient pallet to allow for an add-on to an existing CT system to form a combination PET/CT apparatus. As discussed above, two top detectors are movable and can be arranged around the patient in positions dependent upon the region of interest of the patient being imaged, e.g., for neurological or cardiovascular scans.

Building a large-bore PET system is expensive, but the detector geometries described above allow for a new large-bore system to be built, while maintaining an acceptable cost structure. In particular, the same amount of detector material is distributed differently and more efficiently.

Figure 12A:
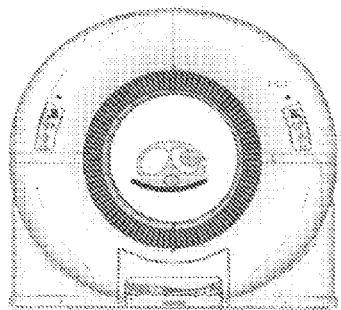
Figure 12B:
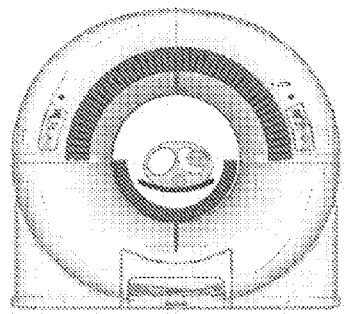

For example, while FIG. 12A shows a conventional approach, FIG. 12B illustrates an embodiment in which the top section is half a ring having a larger diameter, while the bottom section has a reduced diameter. In the alternative embodiment shown in FIG. 12C, the bottom detector section is flat.

The embodiments described above produce substantially (if not exactly) the same image in the same amount of time as the full-ring geometry, but with a reduction of 20% to 50% of the detector material. This increased efficiency can be used to either improve system performance at the same cost, or to reduce the cost for the same imaging performance.

Figure 13:
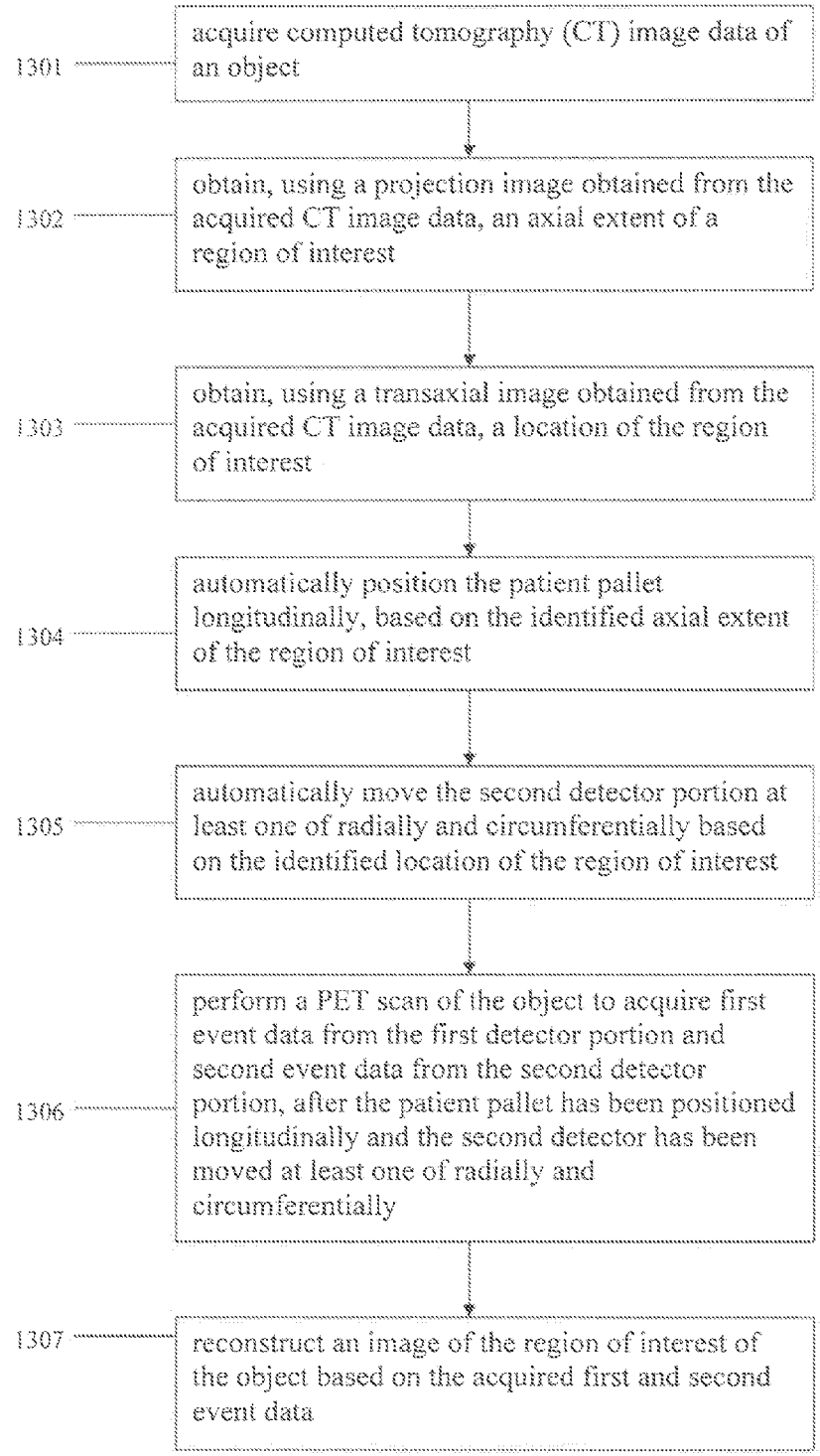
FIG. 13 is a flowchart illustrating steps in a method executed using a PET/CT scanner.

FIG. 13 illustrates, in one embodiment, a method of acquiring imaging data of an object arranged on a patient pallet using a computed tomography (CT) scanner configured to scan the object, and a positron emission tomography (PET) scanner that includes a first detector portion arranged circumferentially around the patient pallet, the first detector portion having a predetermined axial extent and transaxially subtending less than 360 degrees with respect to a central axis of the scanner, and a second detector portion arranged separately from and opposing the first detector section, wherein the second detector portion is configured to be movable radially and circumferentially around the object.

In step 1301, CT image data of the object is acquired using the CT scanner. Alternatively, CT image data acquired at a previous time can be retrieved from a memory.

In step 1302, an axial extent of a region of interest e.g., a patient's heart, breast, or other organ, etc., is obtained using a projection image obtained from the acquired CT image data. For example, a sagittal or coronal CT image can be used to determine the axial extent of the region of interest.

In step 1303, a location (e.g., x-y coordinates of the center) of the region of interest is obtained using a transaxial CT image obtained from the acquired CT image data.

Note that steps 1302 and 1303 can be performed manually by an operator or automatically using image processing software executing on a data processing system.

In step 1304, the patient pallet is automatically positioned longitudinally, based on the obtained axial extent of the region of interest and the current position of the patient on the pallet. As discussed below, a controller can send a command to a mechanical subsystem to move the patient pallet longitudinally to better image the region of interest using a PET scan.

Figure 9:
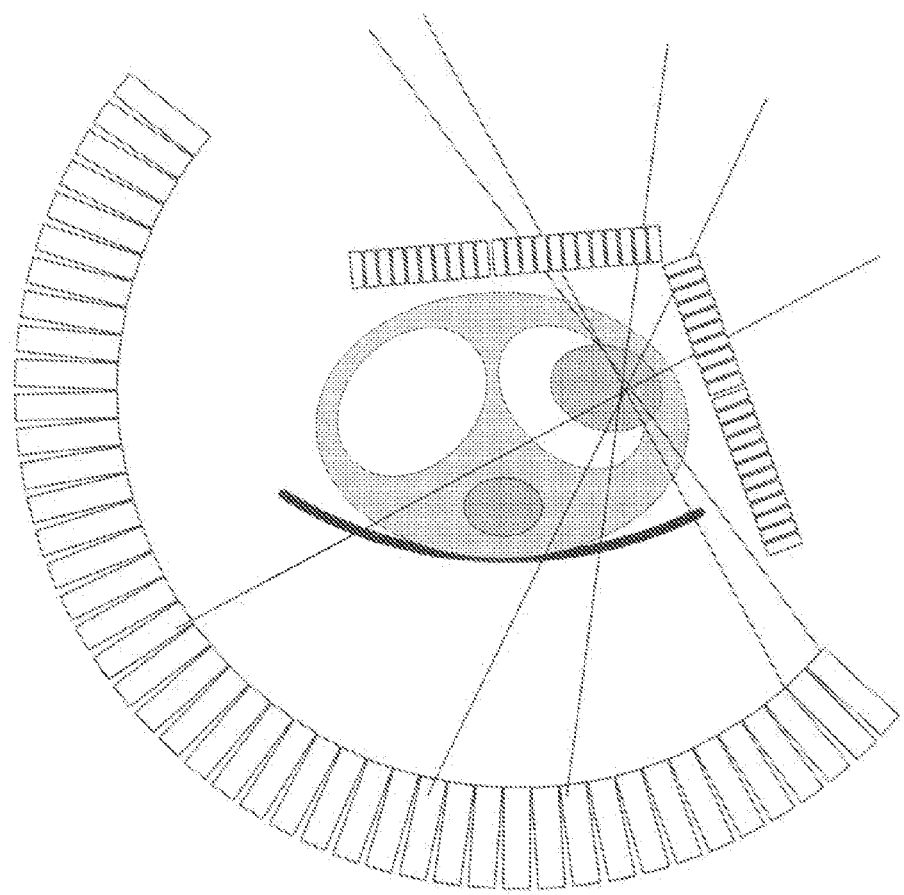

In step 1305, the second and third detector portions are automatically moved at least one of radially and circumferentially based on the obtained location of the region of interest. See, e.g., FIGS. 9 and 10A. Depending on which organ will be imaged using the PET scan, i.e., the location of the region of interest, the controller causes a detector positioning unit to reposition the second and/or third detector portions.

In step 1306, after the patient pallet has been positioned longitudinally and the second and third detectors have been moved at least one of radially and circumferentially, a PET scan of the object is performed to acquire first event data from the first detector portion, second event data from the second detector portion, and/or third event data from the third detector portion.

In step 1307, a PET image of the region of interest of the object is reconstructed by a data processing system based on the acquired first, second, and or third event data.

Figure 14:
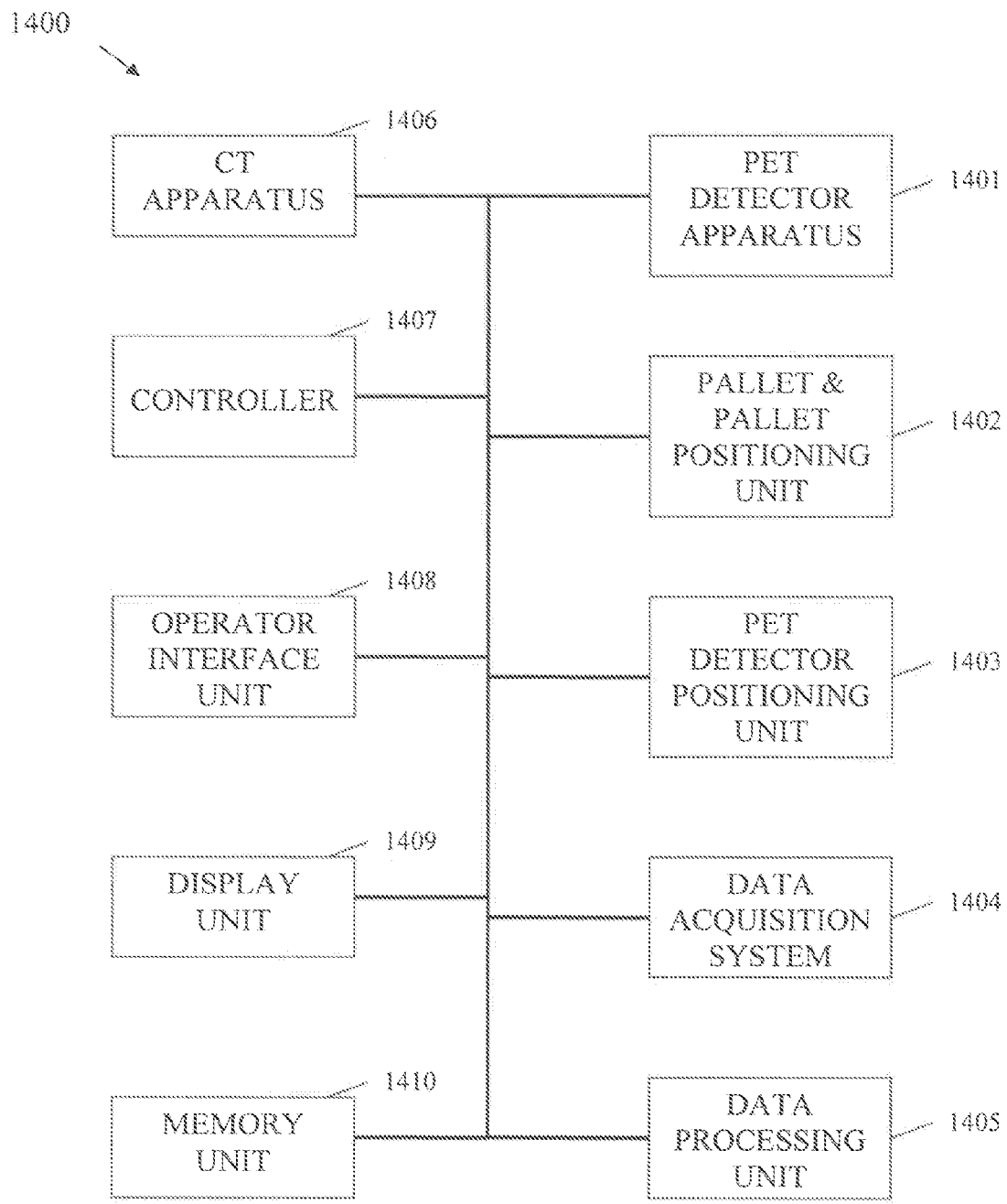
FIG. 14 illustrates a system according to one embodiment.

FIG. 14 illustrates a PET/CT system 1400 according to one embodiment, the system including a CT apparatus 1406 and a PET detector apparatus 1401.

Figure 12C:
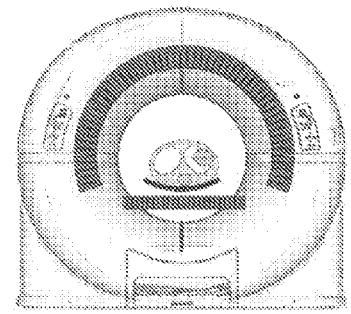

The PET detector apparatus 1401 includes, for example, the detector arrays shown in FIG. 11 or FIGS. 12B-12C. Further, the system 1400 includes a movable patient pallet 1402 that includes a pallet positioning unit configured to position the patient pallet within the PET detector apparatus 1401 and the CT apparatus 1406, based on, for example, commands received from the controller 1407.

The controller 1407 controls the overall functioning of the PET/CT system 1406, including controlling the position of the patient pallet via the pallet positioning unit. The pallet positioning unit includes mechanisms configured to move the patient pallet at least in a longitudinal direction.

The controller 1407 also controls the PET detector positioning unit 1403, which positions one or more PET detector portions around a patient on the pallet. For example, as shown in FIG. 11, the PET detector positioning unit 1403 includes mechanisms configured to move the one or more "top" detector arrays both circumferentially and radially around the patient, based on a region of interest of the patient being imaged.

As shown in the flowchart of FIG. 13 and described above, the controller 1407 sends commands to the pallet positioning unit 1402 and the PET detector positioning unit 1403 to position the pallet and the detectors prior to a PET scan, based on positioning information obtained from a CT scan of the patient and the current position of the pallet and the detectors.

The data acquisition system 1404 obtains PET event data from the PET detector apparatus 1401 during a PET scan and sends the event data to the data processing unit for reconstruction of a PET image. The PET event data can also be stored in the memory unit 1410 prior to processing by the data processing unit 1405.

The operator interface unit 1408 is configured to receive operator commands, for example, initiating a CT scan or a PET scan or setting a region of interest on a CT image, and/or to receive parameters associated with the scans. PET and CT images of the patient, as well as operational parameters associated with the scans are displayed on the display unit 1409.

As one of ordinary skill in the art would recognize, the controller 1407 and the data processing unit 1405 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog or any other hardware description language and the code may be stored in an electronic memory directly within the FPGA or CPLD, or as a separate electronic memory. Further, the memory unit 1410 may be non-volatile, such as ROM, EPROM, EEPROM or FLASH memory. The memory unit 1410 can also be volatile, such as static or dynamic RAM, and a processor, such as a microcontroller or microprocessor, may be provided to manage the electronic memory as well as the interaction between the FPGA or CPLD and the memory unit.

Alternatively, the CPU in the controller 1407 or the data processing unit 1405 may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art.

Once processed by the data processing unit 1405, the processed signals are stored in memory unit 1410, and/or displayed on display unit 1409. As one of ordinary skill in the art would recognize, memory unit 1410 can be a hard disk drive, CD-ROM drive, DVD drive, FLASH drive, RAM, ROM or any other electronic storage known in the art. Display unit 1409 can be implemented as an LCD display, CRT display, plasma display, OLED, LED or any other display known in the art. As such, the descriptions of the memory unit 1410 and the display unit 1409 provided herein are merely exemplary and in no way limit the scope of the present advancements.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An imaging system, comprising:
   a computed tomography (CT) scanner configured to scan an object arranged on a patient pallet;
   a positron emission tomography (PET) scanner, including
      a first detector portion, including first detector elements, arranged circumferentially around the patient pallet, the first detector portion having a predetermined axial extent and transaxially subtending less than 360 degrees with respect to a central axis of the scanner; and
      a second detector portion, including second detector elements, arranged separately from and opposing the first detector portion, wherein the second detector elements are of a different type than the first detector elements, and the second detector portion is configured to be movable radially and circumferentially around the object;
   a controller configured to
      cause the CT scanner to scan the object to obtain CT image data of the object;
      obtain a location of a region of interest obtained using a transaxial image obtained from the CT image data; and
      automatically cause the second detector portion to be moved at least one of radially and circumferentially based on the identified location of the region of interest; and
   an acquisition subsystem configured to acquire first event data from the first detector portion, to acquire second event data from the second detector portion, and to transmit the acquired first and second event data to a data processing system for analysis and reconstruction.

2. The imaging system of claim 1, wherein the controller is further configured to:
   obtain an axial extent of the region of interest within the object using a projection image obtained from the CT image data; and
   cause the patient pallet to be positioned longitudinally based on the obtained axial extent of the region of interest.

3. The imaging system of claim 2, wherein the controller is further configured to cause a PET scan of the object to be performed after the patient pallet has been positioned longitudinally and the second detector portion has been moved at least one of radially and circumferentially.

4. The imaging system of claim 2, further comprising:
   a mechanical subsystem configured to move the patient pallet longitudinally in response to a command received from the controller.

5. The imaging system of claim 1, further comprising:
   a detector positioning unit configured to move the second detector portion at least one of radially and circumferentially in response to at least one command received from the controller.

6. The imaging system of claim 1, further comprising:
   the data processing system configured to reconstruct an image of the region of interest of the object based on the acquired first and second event data.

7. The imaging system of claim 1, wherein the PET scanner further comprises:
   a third detector portion, including third detector elements, arranged separately from and opposing the first detector section, wherein the third detector elements are of a different type than the first detector elements, and the third detector portion is configured to be movable radially and circumferentially around the object,
   wherein the acquisition subsystem is configured to acquire third event data from the third detector portion, and to transmit the acquired first, second, and third event data to the data processing system for analysis and reconstruction.

8. A method of acquiring imaging data of an object arranged on a patient pallet using a computed tomography (CT) scanner configured to scan the object, and a positron emission tomography (PET) scanner that includes a first detector portion arranged circumferentially around the patient pallet, the first detector portion having a predetermined axial extent and transaxially subtending less than 360 degrees with respect to a central axis of the scanner, and a second detector portion arranged separately from and opposing the first detector section, wherein the second detector portion is configured to be movable radially and circumferentially around the object, the method comprising:
   acquiring CT image data of the object;
   obtaining, using a projection image obtained from the acquired CT image data, an axial extent of a region of interest;
   obtaining, using a transaxial image obtained from the acquired CT image data, a location of the region of interest;
   automatically positioning the patient pallet longitudinally, based on the obtained axial extent of the region of interest; and
   automatically moving the second detector portion at least one of radially and circumferentially based on the obtained location of the region of interest.

9. The method of claim 8, further comprising:
   performing a PET scan of the object to acquire first event data from the first detector portion and second event data from the second detector portion, after the patient pallet has been positioned longitudinally and the second detector has been moved at least one of radially and circumferentially.

10. The method of claim 9, further comprising:
    reconstructing an image of the region of interest of the object based on the acquired first and second event data.

* * * * *